US011185348B2

United States Patent
Feskov et al.

(10) Patent No.: US 11,185,348 B2
(45) Date of Patent: *Nov. 30, 2021

(54) METHOD OF IN VITRO FERTILIZATION WITH DELAY OF EMBRYO TRANSFER AND USE OF PERIPHERAL BLOOD MONONUCLEAR CELLS

(71) Applicant: PROGENA INC., Bryn Mawr, PA (US)

(72) Inventors: Alexander Feskov, Kharkov (UA); Irina Feskova, Kharkov (UA); Ievgeniia Zhylkova, Kharkov (UA); Stanislav Zhilkov, Philadelphia, PA (US)

(73) Assignee: PROGENA INC., Bryn Mawr, PA (US)

( * ) Notice: Subject to any disclaimer, the term of this patent is extended or adjusted under 35 U.S.C. 154(b) by 196 days.

This patent is subject to a terminal disclaimer.

(21) Appl. No.: 16/160,436

(22) Filed: Oct. 15, 2018

(65) Prior Publication Data
US 2019/0110813 A1  Apr. 18, 2019

Related U.S. Application Data

(62) Division of application No. 13/655,257, filed on Oct. 18, 2012, now Pat. No. 10,271,876.

(60) Provisional application No. 61/629,651, filed on Nov. 23, 2011.

(51) Int. Cl.
| A61B 17/435 | (2006.01) |
| A61D 19/04 | (2006.01) |
| A61K 35/14 | (2015.01) |
| C12N 5/078 | (2010.01) |
| A61D 19/00 | (2006.01) |
| A61K 35/12 | (2015.01) |

(52) U.S. Cl.
CPC ............ *A61B 17/435* (2013.01); *A61D 19/00* (2013.01); *A61D 19/04* (2013.01); *A61K 35/14* (2013.01); *C12N 5/0634* (2013.01); *A61K 2035/124* (2013.01); *C12N 2501/31* (2013.01)

(58) Field of Classification Search
CPC ..... A61B 17/425; A61B 17/43; A61B 17/435; A61K 35/14
See application file for complete search history.

(56) References Cited

U.S. PATENT DOCUMENTS

| 2003/0109042 A1* | 6/2003 | Wu .......................... A61P 37/00 435/372 |
| 2005/0118563 A1 | 6/2005 | Sher et al. |
| 2005/0241013 A1 | 10/2005 | Sher et al. |
| 2006/0015961 A1 | 1/2006 | Tilly et al. |
| 2007/0010013 A1 | 1/2007 | Bukovsky et al. |
| 2009/0053182 A1* | 2/2009 | Ichim ................... A61K 38/193 424/93.7 |
| 2009/2392071 | 9/2009 | Leese et al. |
| 2010/0239539 A1* | 9/2010 | Sing ........................ A61K 35/50 424/93.7 |

FOREIGN PATENT DOCUMENTS

| JP | 2004275145 | * 10/2004 | ............ C12N 5/0647 |
| WO | WO 2003/022302 | 3/2003 | |

OTHER PUBLICATIONS

Koldehoff et al.,—"Modulating impact of human chorionic gonadotropin hormone on the maturation and function of hematopoietic cells", Journal of Leukocyte Biology, vol. 90, Nov. 2011, pp. 1017-1026.

Guerin et al.—"Regulatory T-cells and immune tolerance in pregnancy: a new target for infertility treatment?" Human Reproduction Update. vol. 1, No 1, pp. 1-19, 2009.

Audus et al.—"Characteristics of the Fetal/Maternal Interface with Potential Usefulness in the Development of Future Immunological and Pharmacological Strategies", The Journal of Pharmacology and Experimental Therapeutics, vol. 301, No. 2. p. 402-409. 2002.

Alexander et al.—"HCG Secretion by Peripheral Moronuclear Cells During Pregnancy", Domestic Animal Endocrinology, vol. 15(5) pp. 377-387, 1998.

International Search Report and Written Opinon dated Feb. 5, 2013 issued in PCT/US2012/066258.

Nakayama, et al., "Human peripheral blood mononuclear cells (PBMC) in early pregnancy promote emryo invasion in vitro: HCG enhances the effects of PBMC," *Human Reproduction*, vol. 17, No. 1, pp. 207-212, 2002.

Jansky, et al., "Dynamics of Cytokine Production in Human Peripheral Blood Mononuclear Cells Stimulated by LPS or infected by *Borrella*," *Physiological Research*, vol. 52, pp 593-598, 2003.

Yoshioka, et al., "Intrauterine administration of autologous peripheral blood mononuclear cells promotes implantation rates in patients with repeated failure of IVF—embryo transfer," *Human Reproduction*, vol. 21, No. 12, p. 3290-3294, 2006.

Fujiwara, H., "Do circulating blood cells contribute to maternal tissue remodeling and embryo—maternal cross-talk around the implantaton period?", *Molecular Human Reproduction*, vol. 15, No. 6, pp. 335-343, 2009.

(Continued)

*Primary Examiner* — Carrie R Dorna
(74) *Attorney, Agent, or Firm* — Oblon, McClelland, Maier & Neustadt, L.L.P.

(57) ABSTRACT

A method of in vitro fertilization wherein the embryo is implanted into the uterus of a female patient at least two, and preferably three to twelve months after the eggs are retrieved from the patient in order to reduce the effect of autoimmune rejection of the embryo by the patient's autoimmune system and increase the probability and success of pregnancy and wherein prior to embryo implantation, the endometrium in the uterus is prepared for embryo implantation by introducing peripheral blood mononuclear cells (PBMCs) into the uterus. The procedure is combined with cryopreservation techniques to preserve the oocytes or the IVF-produced embryos of the patient.

2 Claims, No Drawings

(56) References Cited

OTHER PUBLICATIONS

Sato, K. et al., "Impact of culture medium on the expansion of T cells for immunotherapy," *Cytotherapy*, vol. 11. No. 7, pp. 936-946, 2009.
Feskov, O., et al., "Investigation of Influence of Intrauterus Peripheral Blood Mononuelear Cells Applicalion on Embryo Implantation Rates for Patients during infertility Curing by IVF Method," 2010.
Feskov. O., et al., "The Influence of Intrauterine Administration of Peripheral Blood Mononuclear Cells on Implantation Rates in "Fresh" and "Cryo" IVF Programs," 2011.
Ideta, A., et al., "Administration of peripheral blood mononuclear cells into the uterine horn to improve pregnancy rate followng bovine embryo transfer," *Animal Reproduction Science*, vol. 117, pp. 18-23, 2010.
Okitsu, O., et al. "Intrauterine administration of autologous peripheral blood mononuclear cells increases clinical pregnancy rates in frozen/thawed embryo transfer cycles of patients wih repeated implantation failure," *Journal of Reproductive Immunology*, vol. 92, pp. 82-87, 2011.
Alexander et al, "HCG Secretion by Peripheral Mononuclear Cells During Pregnancy", *Domestic Animal Endocrinology*, 1998, vol. 15, No. 5, pp. 377-387
Y. M. Zhang et al, "Macrophages in Human Reproductive Tissues Contain Luteinizing Hormone/Chorionic Gonadotropin Receptors", *Am J Reprod Immunology*, 2003, vol. 49, Issue 2, p. 93-100 Abstract only 1 page https://onlinelibrary.wiley.com/doi/abs/10.1034/j.1600-0897.2003.00013.x.
Zygmunt et al, "HCG increases trophoblast migration in vitro via the insulin-like growth factor-11/mannose-6 phosphate receptor", *Molecular Human Reproduction*, 2005, vol. 11, No. 4, pp. 261-267.
Zhang et al, Negative regulatory role of mannose receptors on human alveolar macrophage proinflammatory cytokine release in vitro, *Journal of Leukocyte Biology*, 2005, vol. 78, 665-674.
Schumacher et al, "Human Chorionic Gonadotropin Attracts Regulatory T Cells into the Fetal-Maternal interface during Early Human Pregnancy", "*Journal of Immunology*", 2009, vol. 182, pp. 5488-5497.
Kane et al., "Proliferation of uterine natural killer cells is induced by hCG and mediated via the mannose receptor", *Endocrinology*, 2009, vol. 150, No. 6, (13 pages).
Evans et al, "Too much of a good thing? Experimental evidence suggests prolonged exposure to hCG is detrimental to endometrial receptivity", *Human Reproduction*, 2013, vol. 28, No. 6, pp. 1610-1619.
Thiruchelvam et al., "The importance of the macrophage within the human endometrium", *Journal of Leukocyte Biology*, 2013, vol. 93, pp. 217-225.
Liang et al., "The high concentration of progesterone is harmful for endometrial receptivity and decidualization", www.nature.scientificreports published online Jan. 15, 2018 . . . (12 pages).
Supplemental Search Report dated Jul. 16, 2020, in European patent application No. EP 17 8473006.2 ( 10 pages).
Examination report No. 2, for standard patent application dated Sep. 1, 2020, in Australian patent application No. 2018203649 (3 pages).
Thompson et al., "Gonadotrotrophin requirements of the developing follicle", *Fertility and Sterility*, 1995, vol. 63, No. 2, pp. 273-276.
Abstracts of the 3 5th Annual Meeting of the ESHRE, Vienna, Austria Jun. 24-26, 2019, i337-i338, (5 pages).
Anette Kullmann, et al., *Avoid Artifacts: Isolate Pure and Funotional Monooyres from PBMC, Buffy Coat or Whole Blood usinq Dynabeads® FlowComp™*, http://tools.thermofisher.com/content/sfs/posters/Human-CD-14.pdf. created Jan. 15. 2010, accessed Sep. 16, 2020 (1 page).
Noorhasan et al. "Serum hCG Levels following the Ovulatory Injection: Associations with Patient\Weight and Implantation Time", Oct. 8, 2015, Hindawi Publishing Corporation Obstetrics and Gynecology International, vol. 2015, pp. 1-6.
Kosaka et al. "Human Chorionic Gonadotropin (HCG) Activates Monocytes to Produce Interleukin-8 via a Different Pathway from Luteinizing Hormone/HCG Receptor System," Nov. 2002, J Clin Endocrinol Metab, 87(11 ):pp. 5199-5208.
Mansour et al. "Intrauterine injection of human chorionic gonadotropin before embryo transfer significantly improves the implantation and pregnancy rates in in vitro fertilization/intracytoplasmic sperm injection: a prospective randomized study," Dec. 6, 2011, Fertility and Sterility, vol. 96, No. 6, pp. 1-6.

\* cited by examiner

METHOD OF IN VITRO FERTILIZATION WITH DELAY OF EMBRYO TRANSFER AND USE OF PERIPHERAL BLOOD MONONUCLEAR CELLS

PRIOR APPLICATIONS

This application is a divisional of U.S. application Ser. No. 13/655,257, filed on Oct. 18, 2012, and claims the benefit of prior-filed U.S. Provisional Patent Application Ser. No. 61/629,651, filed on Nov. 23, 2011, the subject matter of which is hereby incorporated by reference in its entirety.

STATEMENT REGARDING FEDERALLY SPONSORED RESEARCH OR DEVELOPMENT

The present invention was not developed with the use of any Federal Funds, but was developed independently by the listed inventors.

FIELD OF THE INVENTION

The present invention relates to the field of in vitro fertilization, specifically in women who have reduced fertility as a result of autoimmune reactions. Disclosed is a method used to enhance the rate and stability of pregnancy inception by combining in vitro fertilization techniques, optionally with prolonged cryopreservation of their oocytes or IVF-produced embryos, combined with controlled preparation of the endometrium in the uterus by means of peripheral blood mononuclear cells (PBMCs) prior to embryo transfer.

BACKGROUND OF THE INVENTION

The World Health Organization reports that each year, more than 15% of women worldwide experience difficulties getting pregnant and seek medical assistance (WHO 1997), estimated to be 60 to 80 million women around the world a decade ago. Infertility is generally defined by the World Health Organization as a lack of conception after an arbitrary period of twelve months. However, many couples attempt for years to conceive naturally before seeking medical assistance in an effort to become pregnant. A decrease in fertility rate is associated with medical and non-medical factors. For example, women's age has been shown to be a direct major determinant of the average time required to conceive. It has been shown that premature ovarian failure occurs in 1:1000 women before the age of 30; 1:250 women by 35 years; and 1:100 by the age of 40. Therefore, the highest birth rates are in the age group of 25-30 years and declines sharply after the age of 35 years. Infertility is currently one of the most frequent health concerns facing the population aged 25-45 years. Thus, great interest and need exist for a method of extending fertility in healthy women, possibly taking away age-related barriers to childbearing, and for women who are unable to conceive through natural methods. Although infertility itself may not threaten physical health, it often has a serious impact on the emotional, mental and spiritual well-being of women and of couples.

Assisted reproductive technologies are procedures that involve extracorporeal handling of both human eggs (oocytes or ova) and sperm (spermatozoa), and of embryos for the purpose of establishing a pregnancy in a female subject. These procedures include, but are not limited to, in vitro fertilization ("IVF") including embryo transfer, gamete intrafallopian transfer, zygote intrafallopian transfer, tubal embryo transfer, gamete and embryo cryopreservation, oocyte and embryo donation, and gestational surrogacy. In vitro fertilization ("IVF") has evolved as the major treatment for infertility or sub-fertility when other methods of assisted reproductive technology have failed. In its most basic sense, the process involves extracting the female egg from a woman and fertilizing the egg by sperm outside the body ("in vitro"). The process involves monitoring a woman's ovulatory process, removing multiple eggs from the woman's ovaries and letting sperm fertilize the eggs in a fluid medium in a laboratory. The eggs are usually retrieved from the patient by transvaginal oocyte retrieval involving an ultrasound-guided needle piercing the vaginal wall to reach the ovaries. Through this needle, follicles can be aspirated, and the follicular fluid is handed to the IVF laboratory to identify and diagnose the ova. It is common to remove between ten and thirty eggs from each patient. The fertilized egg, (embryo), or usually multiple embryos, are then transferred to the patient's uterus with the intention of establishing a successful pregnancy. See, for example, U.S. Pat. No. 7,781,207.

First developed in the 1970's, in vitro fertilization has provided an effective form of assistance for a large proportion of women to date. Currently, it is reported that IVF accounts for 1.3% of all live births in Europe [Nygren et al. 2001] and 1.7% of all live births in Australasia [Hurst et al. 2001.] In the United States, assisted reproductive technology IVF cycles started in 2006 resulted in 41,343 births (54,656 infants), which was slightly more than 1.0% of total US births that year. In 2010, Robert Edwards was awarded the Nobel Prize in Physiology or Medicine for the development of in vitro fertilization. The next step was the ability to freeze and subsequently thaw and transfer embryos, first pioneered by Carl Wood, which significantly improved the feasibility of IVF treatment.

Typical successful pregnancy rates obtained with previous in vitro fertilization techniques remain relatively low, in the range of 15% to 25%, based on a number of reported studies. It is widely accepted by health care professionals that the most significant limiting factor to fertilization is the failure of embryos to implant into the endometrium, the lining of the uterus. Blake et al. report that 80-85% of embryos fail to result in pregnancy following transfer into IVF patients resulting in an enormous wastage of embryos. Simon et al. demonstrated that in women undergoing IVF cycle, implantation was detected in 60% of the cycles, therefore in all embryos transferred during IVF, 40% fail to implant.

One possible reason for low implantation rates during IVF is that embryos are transferred to the uterus two days after fertilization at the 4-8 cell stage. One view is that it may be more desirable to use embryos at the blastocyst stage reached at day 5-7 of culture. The advantages suggested include improved synchronization between embryo and uterus and the ability to select better quality embryos over the longer culture period. Blastocyst transfer may also help reduce the number of multiple births resulting from IVF by allowing the selection of fewer numbers of highly competent embryos per transfer. Typically during IVF procedure, two to five embryos are transferred to the uterus in order to increase the chance of implantation, creating the risk of multiple pregnancies. Consequently, more than half of all babies born in the United States after IVF treatment result from multiple gestations. It is sometimes the case that multiple implantations occur in the uterus and as the embryos continue to grow and develop within the womb, the patient is unable to carry more than one or two fetuses to term. At that point, a difficult decision is made to terminate those pregnancies and withdraw the additional fetus or fetuses from the womb, a process called embryo or fetus reduction, a procedure to reduce the number of viable embryos or fetuses in a multiple pregnancy. Such decisions carry with them both ethical and often psychologically traumatic implications. Development of laboratory techniques which would increase the probability and certainty of implantation of each embryo are still desired for a number of the aforementioned reasons.

In a process called natural cycle in vitro fertilization, the fertilization is performed by collecting one or more naturally selected eggs from the patient during a woman's natural menstrual cycle without the use of any drugs. In modified natural cycle IVF, fertility medication is used for two to four days during a woman's natural cycle to avoid spontaneous ovulation and to make the treatment more successful. "Mild IVF" is a method where a small dose of ovarian stimulating drugs are used for a short duration during a woman's natural cycle aimed at producing 2-7 eggs and creating healthy embryos. This method appears to reduce complications and side-effects for women and it is aimed at quality, and not quantity of eggs and embryos. However, this method yields a very low success rate of pregnancy.

Additional techniques are therefore used routinely in order to increase the chance of pregnancy. The most common is ovarian hyperstimulation or super-ovulation that is used in order to stimulate the ovaries to produce multiple eggs that are then retrieved from the patient. The long protocol typically involves downregulation (suppression or exhaustion) of the pituitary ovarian axis by the prolonged use of a gonadotropin releasing hormone (GnRH) agonist. Subsequent ovarian hyperstimulation, typically using follicle stimulating hormone (FSH), starts once the process of downregulation is complete, generally after 10 to 14 days. An IVF cycle using this protocol is known as conventional in vitro fertilization. The short protocol skips the downregulation procedure, and consists of a regimen of fertility medications to stimulate the development of multiple follicles of the ovaries. Other procedures use gonadotrophin-releasing hormone agonists (GnRHA), which decreases the need for monitoring by preventing premature ovulation, and more recently gonadotrophin-releasing hormone antagonists (GnRH Ant) have been used, which have a similar function. In most patients, injectable gonadotropins (usually FSH analogues) are used under close monitoring. Such monitoring frequently checks the estradiol level of the patient and, by means of gynecologic ultrasonography, follicular growth. Typically, approximately 10 days of injections are necessary. Ovarian stimulation carries the risk of excessive stimulation leading to ovarian hyperstimulation syndrome (OHSS), a potentially life-threatening complication of abdominal distension, ovarian enlargement, and respiratory, hemodynamic and metabolic complications. In addition, it has also of recent been demonstrated that fertility drugs used for the stimulation of ovulation of patients undergoing IVF treatment contribute to compromised implantation receptivity of the embryo in the uterus and lead to a decreased rate of pregnancy inception. [Ertzeid et al. 2001].

Female fertility can be affected by dysfunctions of the reproductive tract, of the neuroendocrine system or of the immune system. Some female cancer patients risk losing their fertility because certain kinds of chemotherapy treatments, and certain types of radiation treatments, can bring on premature menopause rendering them sterile. In Western Europe and North America, endocrine dysfunction is identified in about 10 to 20% of women presenting with infertility [Crosignani et al. 2000] Still, in about 10 to 20% of cases, the cause of infertility remains unknown. It is postulated that autoimmune reactions of the body may be the cause of infertility in many such women. Reproductive autoimmune failure and defects can be associated with overall activation of the immune system or with immune system reactions that are specifically directed against ovarian antigens.

Haller-Kikkatalo explains that active tolerance mechanisms are required to prevent self-protective inflammatory responses in the human body to the many foreign air-borne and food antigens that are encountered at the body's mucosal surfaces. However, the most important aspect of tolerance is self-tolerance, which prevents the body from mounting and immune attack against its own tissues—this is the prevention from autoimmune reactions. Autoimmunity is associated with an imbalance of various components of immune response and with the development of autoantibodies directed against normal host antigens. Female fertility is regulated by a series of highly coordinated and synchronized interactions in the hypothalamic-pituitary-ovarian axis. Reproductive autoimmune failure syndrome was originally described by Gleicher et. al. in women with endometriosis, infertility and increased autoantibodies. Although the impact of particular autoantibodies on the pathogenesis of infertility is not yet uniformly understood, autoimmune mechanisms as well as an increased production of multiple autoantibodies are involved in such infertility disorders as premature ovarian failure (POF), subclinical ovarian failure, recurrent pregnancy loss, endometriosis, polycystic ovary syndrome (PCOS), unexplained infertility, repeatedly unsuccessful IVF attempts, and spontaneous abortions. Some studies have suggested the lesser importance of specific antibodies and stressed the key role of overall activation of the immune system in reduced fecundity. [N. Gleicher, 2001; Dmowski et al., 1995.]

A group of research has focused on developing approaches to overcome immune-related infertility. The first and most commonly used approach is the use of medications that aim to suppress the autoimmune response in the patient in order to allow inception of pregnancy. For example, low dose oral prednisolone therapy was suggested for improving pregnancy rate in patients with recurrent IVF failure. However, contradicting data exist indicating that certain antibodies damage the embryo, interfere with the implantation process or interfere with the formation of the placenta. This renders it difficult to predict the success of therapy using these particular immunosuppressive medications. Methods have developed using milder pretreatment with acetylsalicylic acid or heparin. However, though this treatment has become generally universal, the rate of pregnancy using this approach remains relatively low. [Maghraby et al., 2007]

A second approach has recently been introduced. The procedure involves the preparation both of the endometrium and its surrounding environment by means of peripheral blood mononuclear cells (PBMCs). [Fujiwara et al., Kosaka et al., Yoshioka et al.] Peripheral blood mononuclear cells (PBMCs) allow the endometrium of the uterus to grow in sufficient size prior to embryo implantation and also act as building blocks by the body for growing the embryo(s) after their implantation in the uterus of the woman. According to proponents, PBMCs have been identified as multipotent cells. Multipotent cells produce cells of a particular lineage or closely related family. They have been shown to have the capability to be naturally transformed into any kind of human tissue. Multipotent cells are a valuable resource for research and therapeutic treatments. Recent advances in bioengineering are quite promising in repairing, building, engineering, regenerating, generating and growing tissue.

European Pat. Application EP1581637 discloses monocyte derived adult stem cells that are isolated from peripheral blood of mammals and methods of preparing, propagating and using these stem cells. The inventors of U.S. Pat. No. 7,795,018, M. Kuwana and H. Kodamo, disclose monocyte-derived multipotent cells (MOMCs) that can differentiate into endothelial cells by a medium culture under conditions inducing differentiation into endothelium. Further disclosed is a method for preparing MOMCs involving culturing PBMCs in vitro on fibronectin and collecting fibroblast-like cells. It was demonstrated that by culturing in a EBM-2 medium, a maintenance medium of endothelial cells, for seven days, MOMCs differentiate into endothelial cells changing the cell's morphology from a spindle shape to a morphology having multiple projections (see U.S. Pat. No. 7,795,018). The researchers of the present invention hypothesized that the use of PBMCs can therefore be instrumental during the reproductive process and have incorporated the use of PBMCs into a novel technique of in vitro fertilization provided herein.

A group of various inception agents has been developed, which separately or in combination, can be applied during IVF treatment in order to promote the acceptance of the embryo by a woman's immune system. Among these agents, soluble human leukocyte antigen G (sHLA-G) appears to be promising. The s-HLA class of molecules has been recognized to be involved in immune response and in the modulation of the maternal-fetal immune relationship during pregnancy. Sher et al. in U.S. patent application Ser. No. 10/829,081 discloses having isolated sHLA-G from the culture media surrounding pooled developing embryos and blastocysts. They observed that the absence of sHLA-G in the supernatant surrounding groups of embryos in culture is associated with significantly reduced IVF implantation and pregnancy rates. They proposed that addition of sHLA-G to the medium in which embryos are cultured and/or delivered into the uterine environment through embryo transfer, would enhance implantation and pregnancy potential of those embryos. Though the technique is useful, neither this approach, nor any other alone has solved the problem of autoimmune infertility. It is suggested herein that such inception agents be used in conjunction with the procedure of the invention herein to improve the probability and success of pregnancy inception.

Finally, engineered glycolipid-like molecular constructs have been shown to be capable of modifying the embryos and enhancing the interaction between the embryo and the target tissue, the endometrium. Building of a macro-molecular matrix on the external surface of an embryo and loading of said matrix with certain agents for stimulation of pregnancy inception are the techniques that, according to proponents, will have very broad applications in IVF treatment in the future. Not only has the modification of embryos by this constructive approach been successfully demonstrated in an in-vitro culture system, but animals have given birth to healthy offspring derived from such modified embryos. However, this approach has not yet been tested in clinical trials and remains premature to be considered among current medical tools.

Much research has been directed to procedures for improving the probability of successful pregnancy and birth of a child. Despite the considerable research, technical advances and variations in procedures, the rate of successful pregnancy utilizing IVF treatment still remains on average in the order of 15-25% per cycle. The researchers herein have attempted to address the challenge of embryo implantation and decrease the risk of autoimmune system responses by presenting a solution focusing on stabilizing the interaction between a woman's immune system and the embryo.

SUMMARY OF THE INVENTION

In its broadest sense of the invention, provided is a method of in vitro fertilization for a female patient, the method comprising the steps of introducing into the uterus an effective amount of a composition comprising peripheral blood mononuclear cells, and transferring at least one embryo into the uterus of the patient after a predetermined delay following initiation of the in vitro fertilization of said patient; and wherein the method results in an increase in the probability of implantation of the embryo in the uterus with successful inception of pregnancy when compared to in vitro fertilization methods lacking such steps. The predetermined delay of time is a period of time sufficient to decrease autoimmune rejection of the embryo or the risk of autoimmune response of the patient. The preferred delay of time before embryo transfer is at least two menstrual cycles or two cycles of ovulation of the patient, though the delay will vary from patient to patient and among species, hybrids and varieties of animals. The preferred delay of time in a human patient is three to twelve months.

It is another aspect of the invention that toward the end of the time-delay period, the women's endometrium is prepared in a way so as to optimize the acceptance of the embryo by the uterine cavity. According to the invention, this is accomplished by intrauterine injection of peripheral blood mononuclear cells (PBMCs), most preferably obtained from the patient. It has been observed herein that this method increases the probability of successful pregnancy inception and early pregnancy development. Combining both the time-delay of implantation in conjunction with cryopreservation of the embryo and the PBMCs preparation of the woman's endometrium is the foundation of the present invention.

More particularly, disclosed is a method of in vitro fertilization for a female patient involving the steps of: (a) obtaining at least one oocyte and fertilizing the oocyte with spermatozoa to form a zygote; (b) developing the zygote in vitro to an embryo stage; ((c) cryopreserving the embryo; (d) waiting a predetermined period of time sufficient to decrease the risk of autoimmune response of the patient; (e) extracting a first portion of peripheral blood mononuclear cells (PBMCs) from the blood of the patient 2 to 4 days prior end of waiting period; (f) culturing said first portion of PBMCs in a suitable culture medium c(g) extracting a second fresh portion of PBMCs from the blood of the patient on the last day of the waiting period; (h) combining the cultured first portion of PBMCs with the fresh second portion of PBMCs to obtain a composition comprising fresh and cultured PBMCs; (i) introducing the composition of PBMCs into the uterus of the patient; (j) thawing the embryo from the cryopreserved state; and (k) transferring at least one thawed embryo into the uterus of the patient to effectuate pregnancy.

An additional aspect of the invention is a composition comprising PBMCs, a method for producing the composition and the application of the PBMC composition in IVF treatment and for growing and engineering certain target tissue of an organism, most preferably the endometrium of a female uterus. Such method involves extracting PBMCs from the blood of a patient; propagating a portion of the extracted PBMCs in the presence of 4.8-6.0% carbon dioxide (CO2) at 36.7-37.3° C. in a culture medium containing (i) RPMI 1640 medium with L-glutamine and sodium bicarbonate, (ii) human recombinant albumin and (iii) a promoting agent capable of improving the ability of PBMCs to enhance tissue growth, such as human chorionic gonadotropin (hCG); and combining the fresh and cultured portions of PBMCs to obtain said composition.

DETAILED DESCRIPTION OF THE INVENTION

The present invention will be more clearly understood by defining certain terms that are used and relied upon throughout the specification.

"Blastocyst" is an embryo, five or six days after fertilization, having an inner cell mass, an outer cell layer called the trophectoderm, and a fluid-filled blastocele cavity containing the inner cell mass from which the whole of the embryo is derived. The trophectoderm is the precursor to the placenta. The blastocyst is surrounded by the zona pellucida which is subsequently shed when the blastocyst "hatches." The zona pellucida, composed of a glycoprotein coat, surrounds the oocyte from the one-cell stage to the blastocyst stage of development. Prior to embryo attachment and implantation, the zona pellucida is shed from the embryo by a number of mechanisms including proteolytic degradation. The zona pellucida functions initially to prevent entry into the oocyte by more than one sperm, then later to prevent premature adhesion of the embryo before its arrival into the uterus.

"Cryo-IVF" refers to a process of in vitro fertilization in which the embryo is cryopreserved then thawed prior to embryo transfer or a process in which the oocyte used for fertilization has been previously frozen then thawed. "Fresh-IVF" refers to a process of in vitro fertilization wherein the embryo is not frozen prior to transfer into the uterine cavity and where the oocytes used to prepare the embryo have not previously been frozen.

"Embryo" is the product of the division of the zygote to the end of the embryonic stage, eight (8) weeks after fertilization. The cleavage stage of the embryo occurs during the first three days of culture. "Embryo transfer" is the procedure in which one or more embryos and/or blastocysts are placed into the uterus or fallopian tubes. As such, the terms "blastocyst" and "embryo" are used interchangeably herein for purposes of defining the term "embryo transfer" and in application of the term "embryo transfer" within the scope and application of the invention as described and claimed.

"Endometrium" refers to the tissue lining the internal surface of the uterus, which is composed of a layer of epithelial cells. The embryo first comes into contact with the endometrium and the extracellular matrix (the "mucus") for implantation. The epithelial and underlying stromal cell layer cyclically thickens, secretes mucus and is shed from the body under the hormonal influences of the menstrual cycle. By the term "implantation" herein is meant the attachment and subsequent penetration by the blastocyst (after having shed its zona pellucida), usually into the endometrium. Attachment to the endometrium lining may occur by interaction between the attachment molecules and on or more components of the endometrium, including membranes of the epithelial cells, mucus, mucin components of the mucus, or an exogenously introduced component of the uterus.

"Fertilization" refers to the penetration of the ovum by the spermatozoa and combination of their genetic material resulting in the formation of a zygote. "Initiation of in vitro fertilization" as used herein means the initiation of controlled ovarian stimulation of a female patient, which involves pharmacological treatment in which women are stimulated to induce the development of multiple ovarian follicles to obtain multiple oocytes at follicular aspiration.

"Uterus", commonly referred to as the womb, is the major female hormone-responsive reproductive sex organ of most mammals including humans that contains the cervix at one end while the other is connected to one or both fallopian tubes, depending on the species. The reproductive function of the uterus is to accept a fertilized ovum which passes through the utero-tubal junction from the fallopian tube. It implants into the endometrium, and derives nourishment from blood vessels which develop exclusively for this purpose. The fertilized ovum becomes an embryo, attaches to a wall of the uterus, creates a placenta, and develops into a fetus during gestation until childbirth. As used herein, the term "uterus" incorporates the fallopian tubes for purposes of embryo transfer. The term "uterus" is also used interchangeably herein with the term "uterine cavity," which is the cavity of the body of the uterus.

During IVF treatment, the immune system of a woman experiences a stimulated production and delivery of oocytes. If the IVF-produced embryo is transferred into the uterus cavity shortly after extraction of oocytes, the immune system may generate an overreaction. Such overreaction of the immune system can be the cause of the body's inability to implant the embryo and lead to autoimmune infertility. In its first aspect, the invention presents delaying the introduction of the embryo into the uterus in order to allow the woman's immune system to settle and regain its proper hormonal balance. During the time-delay, the female patient's oocytes or embryos are optionally preserved via cryopreservation.

The time-delay useful in the method of the invention herein is a predetermined amount of time for each specific patient. For human patients, the time delay may be a length of time anywhere of at least two months or two cycles of ovulation. In the preferred embodiment, the predetermined delay is three cycles of ovulation, which typically corresponds to three months. Most women experience one cycle of ovulation every 28 days. It is to be understood, however, that because cycles of ovulation vary from woman to woman, the number of actual days of the delay will vary with each patient in the course of treatment of the IVF procedure of the invention. It is possible that a female patient will experience only two cycles of ovulation within a three-month period, or likewise, that a woman may experience more than three cycles of ovulation within a three-month period. In some cases, it is possible that a patient will not experience any additional ovulation after the initial ovulation post initiation of the IVF treatment. The time delay can also be of duration of more than three months, but will preferably be within three months to one year. It has been demonstrated herein that the predetermined time-delay significantly decreases the risk of autoimmune infertility and, therefore, significantly increases the probability of successful pregnancy Within the scope of the invention are embodiments wherein oocytes or embryos that are derived from a female or females other than the patient are used for pregnancy inception, termed "donor eggs" or "donor embryos", respectively. This would occur in situations where the female patient is not able to ovulate or to produce viable ova, or in which the embryos derived by fertilizing the patient's own eggs are determined to be too deficient for embryo transfer or have a low probability of survival based on either morphological or genetic testing.

In its common technique, women undergoing IVF require hormone injections to stimulate follicular development and multiple egg production. This stimulation process usually requires the initial use of a gonadotropin releasing hormone (GnRH) agonist to suppress ovarian function, preventing ovulation until the desired time. The medication which is most commonly used is clomiphene citrate (Clomid®), a selective estrogen receptor modulator that increases production of gonadotropins by inhibiting negative feedback from estrogen on the hypothalamus. This induction of final maturation and release of oocytes is often induced by administration of luteinizing hormone. Protocols for these injections are well known and established in the art and are utilized in any of the embodiments of the methods of the invention.

According to the method of the invention, unfertilized eggs are harvested and retrieved from the female patient by techniques known in the art. Such techniques involve placing a specially-designed needle into the ovarian follicle and removing the fluid that contains the eggs. Once the follicular fluid is removed from the follicle, the eggs may be inspected microscopically and diagnosed to observe their morphological features. One method for obtaining oocytes for IVF is disclosed in U.S. Pat. No. 4,725,579. In the method herein, six oocytes are gathered from the patient, though preferably four are obtained. The eggs are then placed into an incubator. Conventional insemination or intracytoplasmic sperm injection (ICSI) is used to fertilize the eggs. The type of fertilization used is often based on the male's semen parameters or other factors such as the type of analysis that may be required of the embryo. During conventional insemination, sperm are mixed with the eggs in a culture dish and incubated overnight to undergo the fertilization process. During intracytoplasmic sperm injection, one sperm is directly injected into one egg. With either technique, the eggs are observed the following day to evaluate for cell division. The fertilized eggs, now called embryos, are then placed into specific culture media that promote growth and development.

According to the invention, the IVF-derived oocytes or embryos are grown on suitable culture medium. Available culture media attempt to provide the nutrients needed for cells to grow and develop and seek to duplicate as much as possible the conditions normally occurring within the female reproductive system. Culture media known in the art that are suitable for use for the in vitro support of cell development and growth in laboratory procedures can be used herein. Examples include, but are not limited to human tubal fluid (HTF) (Irvine Scientific), N-2-hydroxyethylpiperazine-N'-2-ethane (HEPES) media (Irvine Scientific), IVF-50 (Scandanavian IVF Science), S2 (Scandanavian IVF Science), G1 and G2 (Scandanavian IVF Science), UniIVF, ISM-1, BlastAssist, UTM media (sold as MEDICULT® media by Origio A/S), Modified Whittens medium, Wittinghams T6 media, Ham's F-10 media, Earle's solution. Buffering systems, such as 4-morpholinepropanesulfonic acid (MOPS) are typically provided. The procedures are well set forth in Trouson et al. (1980 and 1982) and Quinn et al. (1985).

Tissue culture media generally are complicated systems, containing an array of amino acids, vitamins and other constituents. Some media consist of balanced salt solutions supplemented with carbohydrate energy sources such as glucose, pyruvate and lactate. The media can also be supplemented with non-essential amino acids. Components in the medium are often derived from non-human and non-animal sources such as recombinant microorganisms. It is desirable to take steps to reduce the possibility of contamination, such as proper purification and preparation techniques practiced in the art. In addition, media may include antibiotics, such as penicillin or streptomycin to destroy bacteria that might be introduced into the medium during the process of oocyte collection.

During in vivo development within the female reproductive system, the oocyte is originated within and released from the ovary during ovulation and proceeds through the oviduct toward the uterus. The fluid of the oviduct contains a number of components that provide nourishment to the oocyte and its surrounding cumulus cells. Once fertilization occurs, the resulting zygote travels down the oviduct and enters the uterus approximately three days later, undergoing internal transformation and experiencing a changing environment. Significant development changes occur as the zygote/embryo/blastocyst develops. The composition of the fluid surrounding the developing embryo in the uterus is tailored to those changing needs.

No single medium is optimized for supporting the gametes, fertilization, zygote maturation, and embryo development compared to the natural environment of the female reproductive system. Thus a number of specialized media have become available to address the varying stages of embryo development. For example, G1 and G2 media were specifically formulated to meet the physiological needs of the cleavage stage embryo and the embryo in the eight-cell through blastocyst stage of development. U.S. Pat. No. 6,605,468 to Robertson et al. discloses a medium for the propagation of early stage embryos to blastocyst stage. The medium contains an effective amount of granulocyte-macrophage colony-stimulating factor (GM-CSF) to increase the percentage of pre-blastocyst embryos which develop to transfer-ready blastocysts. Also disclosed is a method of growing early stage human embryos to transfer ready blastocysts. The result is that a greater proportion of embryos can be grown to blastocyst stage and be used for implantation in an IVF program. A number of studies have been made using culture techniques whereby the embryos are co-cultured with feeder cells. [Menezo et al., 1990; Planchot et al., 1995] Other stimulatory factors such as cytokines can be added to the medium to propagate embryo growth, such as leukemia inhibitory factor (LIF), see for example U.S. Pat. No. 5,418,159 to Gough et al. Leukemia inhibitory factor is a potent hormone having general utility in the area of in vitro embryology, such as in maintaining embryonic stem cell lines and increasing the efficiency of embryo transfer.

In U.S. Pat. No. 6,838,235, Gardner et al., provide that instead of immersing human reproductive cells in a single culture medium throughout the IVF process, the reproductive cells may be moved through a sequence of distinct culture media as the various IVF procedures are carried out. In one formulation, the culture media is specifically formulated to provide a physical environment similar to that found within the female reproductive tract and conducive to growth and development of embryos. The disclosure suggests that specialized media can be provided for oocyte retrieval and handling; oocyte maturation; ordinary fertilization; oocyte, zygote and embryo examination and biopsy; embryonic development to the eight-cell stage; embryonic development to the blastocyst stage; embryo transfer; and cryopreservation.

In addition to the use of commonly available culture media for embryo preparation, the method of the invention can be combined with other techniques in order to increase the probability and success of pregnancy inception. A number of methods have developed in which the embryo is modified in some way prior to transfer into the uterine cavity. For example, European Pat. App. EP 1765987 (WO 2005121322 A1) discloses enzymatic modification of cell-surface H antigen, by the addition of one or more monosaccharide units generating cells which are serologically equivalent to A or B antigen red blood cells. Research indicates that there is a receptor on the embryo for hyaluronate and that there is also a receptor for hyaluronate on the endometrium of the uterus of the mother. Hyaluronate is thought to act like biological glue that assists the embryo in binding to the endometrium and, accordingly, supports implantation. U.S. Pat. No. 8,183,214 to Carter et al. discloses a method of localizing hyaluronic acid to the surface of a cell or multi-cellular structure (an embryo) for use in IVF procedures. The disclosure provides carbohydrate-lipid constructs that incorporate stably into the lipid bi-layer or membrane of a cell or embryo changing its biological activity in order to improve certain characteristics, such as growth characteristics, storage characteristics, and survival of the embryo and the likelihood of implementation of the embryo following transfer to the uterus. Similarly, U.S. Pat. No. 7,819,796 to Blake et. al. discloses another exogenously prepared construct to enhance the attachment and implantation of an embryo. The embryo is modified by glycolipids having lipid tails that are inserted in to the cell membrane of the embryo or into the zona pellucida in which the glycolipid has been modified to incorporate a binding part wherein the binding part is adapted to enable binding to an attachment molecule. Attachment of the embryo to the endometrium can occur through the binding parts directly or through a bridging molecule. Another method, protein painting, is a method for modifying the external antigens of cell membranes without gene transfer. The specification for international application PCT/US98/15124 (publication WO 99/05255) describes the enhancement of implementation by contacting the embryo with a lipid-modified adhesion molecule so as to modify the development of the embryo. U.S. patent application Ser. No. 13/067,021 describes another non-transgenic method for effective qualitative and/or quantitative changes in the surface antigens expressed by a cell. The synthetic molecule constructs disclosed by the researchers incorporate into the lipid bilayer of the cell, and it is proposed that such insertion is thermodynamically favored. The foregoing methods of embryo preparation, as well as other methods practiced in the art, are contemplated within the scope of the invention herein.

In the traditional IVF process, embryos are transferred to the uterine cavity two days after fertilization when each embryo is at the four (4) cell stage or three days after fertilization when the embryo is at the eight (8) cell stage. It has been recognized that it may be desirable to use embryos at the blastocyst stage when reached at day five to seven of culture. The IVF method of the invention herein allows for embryo transfer at any time along the spectrum of embryo/blastocyst development. Through visual observation, such as by with the use of microscopy, blastocysts or embryos are considered ready to be transferred to the uterus when the blastoceol cavity is clearly evident and comprises greater than 50% of the volume of the embryo. In an in vivo environment, this stage would normally be achieved four to five days after fertilization, soon after the embryo has traversed the fallopian tube and arrives in the uterus.

According to the second aspect of the invention, it has been discovered by the inventors herein that introducing a composition containing peripheral blood mononuclear cells (PBMCs) into the uterus of a female patient prior to embryo transfer during IVF treatment clearly increases the probability of successful embryo implantation in the endometrium of the uterus thus leading to viable pregnancy. Without intending to be bound by scientific theory, it is thought that the PBMCs promote the health and viability of a woman's endometrium and of the transferred embryo.

PBMCs are multipotent progenitor cells that have the potential to give rise to cells from multiple, but a limited number of lineages. At the end of the long series of cell divisions that form the embryo are cells that are terminally differentiated, or that are considered to be permanently committed to a specific function. Stem cell experiments have been able to direct blood stem cells to behave like neurons, or brain cells—a process known as trans-differentiation. The use of pluripotent stem cells from fetuses, umbilical cords or embryonic tissues derived from in vitro fertilized eggs raises ethical and legal questions in the case of human materials, poses a risk of transmitting infections and/or may be ineffective because they may be rejected by a recipient's immune system. Arguably, the use of PBMCs raises less ethical and legal concerns because PBMCs are cells that are obtained from the blood and do not constitute stem cells, while still being able to differentiate.

As used herein, a peripheral blood mononuclear cell (PBMC) is a multipotent cell that is extracted, harvested, derived, isolated or otherwise obtained from the blood of a subject. A PBMC is a blood cell and that has a round nucleus. The PBMC class includes, but is not limited to lymphocytes, a monocytes and macrophages. These blood cells are a critical component in the immune systems of organisms utilized in fighting infection and in operating other functions involving the immune system. The lymphocyte population consists of T cells (CD4 and CD8 positive~75%), B cells and NK cells (~25% combined). The PBMC population also includes basophils and dendritic cells.

PBMCs can be isolated from human peripheral blood by common methods known in the art. The cells can be extracted from whole blood using FICOLL® (GE Healthcare Bio-Sciences AB LLC of Sweden), a hydrophilic polysaccharide that separates layers of blood, which will separate the blood into a top layer of plasma, followed by a layer of PBMCs and a bottom fraction of leukocytes, erythrocytes, and polymorphonuclear cells (such as neutrophils, eosinophils). The polymorphonuclear cells can be further isolated by lysing the red blood cells. Ficoll® is part of Ficoll-Paque® (GE Healthcare Bio-Sciences AB LLC of Sweden). Ficoll-Paque® is normally placed at the bottom of a conical tube, and blood is then slowly layered above the Ficoll-Paque®. After being centrifuged, several layers will be visible in the conical tube, from top to bottom: plasma and other constituents, the layer of mononuclear cells containing the PBMCs, Ficoll-Paque®, and erythrocytes and granulocytes which are present in pellet form. This separation allows easy harvest of the PBMC's. Some red blood cell trapping (presence of erythrocytes and granulocytes) may occur in the PBMC or Ficoll-Paque® layer. Major blood clotting may sometimes occur in the PBMC layer. Ethylene diamine tetra-acetate (EDTA)) and heparin are commonly used in conjunction with Ficoll-Paque® to prevent clotting. Because Ficoll-Paque® layering is a very slow process, devices that aid in the overly, which is most time-consuming step, have been developed. One such a product is SepMate™-50 (StemCell Technology Inc. of Canada), a specialized tube containing a porous insert that forms a physical barrier between the Ficoll-Paque® and blood sample. This allows the blood sample to be rapidly pipetted onto the insert, avoiding the need for overlaying it directly onto Ficoll-Paque®. The SepMate™ insert also reduces the duration of the centrifugation step, and after centrifugation, the top layer containing plasma and PBMCs can be poured into a separate container. Other devices include a column containing a porous high-density polyethylene barrier or "frit." These products allow blood to be layered on much more quickly without mixing polysaccharide and blood. An example of such a product is the "Accuspin System Histopaque-1077" sold by Sigma Aldrich. It is also possible to have the Ficoll-Paque® separating system included in a vacutainer blood collection tube. Such vacutainers increase the convenience and safety of collecting blood products, but are much more costly than the basic vacutainer. Another such product, Floaties™, has been shown to effectively overlay blood or a cellular suspension on Ficoll® using a special mixture of polymer beads or pellets. This product is inexpensive, reduces researcher reliance on technique, and actually speeds up the overlay process. Any of the foregoing techniques, including other techniques that are or will become practiced in art of collecting, isolating, extracting, harvesting, separating, removing, or in any other way obtaining PBMCs from the blood of an organism, human or animal, are contemplated within the scope of the embodiments of the invention herein.

In one of the aspects of the invention, provided herein is a method of culturing the PBMCs cells. The method comprises culturing the cells on fibronectin-coated plates in a humidified atmosphere containing from 4.8% to 6.0% of carbon dioxide ($CO_2$) at a temperature in the range of 36.7° C. to 37.3° C., at a density of 104 to 107/mL. In a preferred embodiment of the method, PBMCs are cultured for a period of time in the range of 46 hours to 72 hours. In a most preferred embodiment, the PBMCs are cultured on fibronectin-coated plates in an atmosphere of 5.0% of $CO_2$ at a temperature of 37.1° C. for 48 hours.

The culture media used herein for propagating the extracted PBMCs is a Roswell Park Memorial Institute medium, commonly known as RPMI medium, available from a number of sources. RPMI medium is often used for cell and tissue culture. RPMI 1640 medium has traditionally been used for the growth of serum-free human lymphoid cells, bone marrow cells and hybridoma cells. RPMI 1640 medium uses a bicarbonate buffering system and differs from most mammalian cell culture media in its pH 8 formulation. The preferred medium according to the methods of the invention utilizes RPMI 1640 culture medium containing L-glutamine and sodium bicarbonate.

According to another aspect of the invention, human recombinant albumin (HRA) is added to the culture medium. HRA is a well-known carrier protein present in high concentrations in plasma with a circulatory half-life of approximately 19 days. It functions in fatty acid transportations to tissues, protein stabilization, binding metal ions to surfaces, and an antioxidative effect in plasma. HRA is widely available from a number of providers, for example from Novozymes, Inc. or Sigma-Aldrich, LLC. The addition of HRA during the method of the invention to the culture medium acts as a food supplement that improves the growth of the PBMCs.

In a further aspect of the invention, human chorionic gonadotropin (hCG) added to the RPMI 1640 culture medium herein. Human chorionic gonadotropin (hCG) is released in the body into maternal circulation during pregnancy by placental synctiotrophoblasts. It has been shown to be an immuno-modulating hormone and reported that administration of hCG increases pregnancy success and antisera to hCG inhibits fetal implantation. hCG interacts with certain receptors (LHCG receptors) and promotes the maintenance of the corpus luteum during the beginning of pregnancy, causing it to secrete the hormone progesterone. Progesterone enriches the uterus with a thick lining of blood vessels and capillaries so that it can sustain the growing embryo and fetus. Due to its highly negative charge, hCG may repel the immune cells of the mother, protecting the fetus during the first trimester. It has also been hypothesized that hCG may be a placental link for the development of local maternal immunotolerance. For example, hCG-treated endometrial cells induce an increase in T cell apoptosis (dissolution of T cells). These results suggest that hCG may be a link in the development of peritrophoblastic immune tolerance, and may facilitate the trophoblast invasion, which is known to expedite fetal development in the endometrium. [Kayisli et al., 2003]. It has also been suggested that hCG levels are linked to the severity of morning sickness in pregnant women. The minimum concentration of the hCG in the culture medium of the invention is not less than 5 IU/mL. For the purpose of clarity, it has been found herein that the hCG in the culture medium prepared according to the method of the invention functions as a promoting agent that improves the ability of PBMCs to enhance tissue growth, specifically the growth of the endometrium during the IVF process of the invention. The cultured PBMCs and/or the combined cultured and fresh PBMC composition have the capability to change the size and receptivity of the patient's endometrial tissue when treated with the PBMC composition of the invention. This results in an increase in the size, specifically an increase in the thickness of the endometrium, as well as an enhanced ability of the endometrium to bind the embryo upon implantation.

The in vitro fertilization method of the invention provides the use of the PBMCs obtained by the above culturing technique in order to improve pregnancy inception. After obtaining oocytes from a female patient, a portion of PBMCs is extracted from the blood of the patient. This portion of PBMCs is then cultured in a suitable culture media according to the method disclosed above to obtain a desirable quantity and quality of PBMCs. After a predetermined waiting or delay period of time discussed herein, an additional portion of blood is obtained from the patient and a fresh portion of PBMCs are extracted from the blood. Alternatively, the lot of blood first obtained from the patient can be divided into various portions containing PBMCs, of which one or some are cultured, and one or some are maintained fresh. The fresh portion is preferably obtained on the last day of the predetermined waiting period of time. Some or all of the fresh PCMBs are then combined with some or the entire cultured portion of PBMCs to obtain a composition that contains both the fresh and the cultured PBMCs. The concentration of PBMCs in a preferred composition of PBMCs of the invention is in the range of 4 to 5 million cells per every milliliter of the composition; however concentrations of up to 8 million cells/mL of the composition are operable within the scope of the invention. The composition can be mixed or blended further or processed in any desirable method so as to combine the PBMCs without damaging the cells. This composition of PBMCs is then introduced, typically via catheter injection, into the uterine cavity of the patient. According to the invention, from 20 to 72 hours later, most preferably 24 hours, one or more embryos are transferred to the uterus for implantation to effectuate pregnancy. The researchers herein have demonstrated that this technique enables the body to utilize the PBMCs as building blocks to increase the thickness of the layer of the endometrium within the uterus and thereby to decrease the risk of failure of pregnancy inception.

It is important that the PBMCs are extracted from the patient herself in the course of the IVF treatment of the invention. However, it is envisioned within the scope of the invention, that the cultured portion of PBMCs can be derived from an individual other than the patient undergoing the in vitro embryo transfer. In such case, the fresh portion of PBMCs is preferably obtained from the patient undergoing embryo transfer so as to address the autoimmune response of the patient.

Preimplantation diagnostics both of embryos and of the patient's reproductive system is another aspect of the present invention. Upon diagnosis of the patient, the thickness of the endometrium, which can be typically measured by ultrasound, is preferred to be in the range of 9 mm to 11 mm at the time of embryo transfer.

Post-implantation diagnostics are also typically performed. Testing to determine whether one or more embryos have implanted into the endometrium, i.e, whether the procedure has resulted in successful pregnancy inception, is performed two weeks after transfer using blood tests on b-hCG (human chorionic gonadotropin), for example, and other techniques commonly known in the art. hCG is essential in the diagnosis of pregnancy and in of pregnancy-related conditions, such as ectopic pregnancy, spontaneous abortion, trisomy 21, molar pregnancy and choriocarcinoma. The event of "biochemical pregnancy" occurs when a pregnancy is diagnosed by detection of hCG in serum or urine that does not develop into a clinical pregnancy. U.S. Pat. No. 4,315,908 to Zer et al. sets forth a method for detecting hCG in the urine by radioimmunoassay. U.S. Pat. No. 8,163,508 to O'Connor et al. provides a method and a kit for predicting pregnancy in a subject by hCG method by determining the amount of an early pregnancy associated isoform of hCG in a sample. Such methods of diagnosis and others are useful within the scope of the invention.

Clinicians strive to identify those embryos for transfer that are most likely to achieve a viable pregnancy. In certain embodiments, the present in invention provides for morphological, genetic and kinetic testing of the oocytes, blastocysts or embryos retrieved from the patient and prepared in vitro. Methods of diagnosis include microscopic physical analysis of the embryo to identify those embryos which appear to be developing normally by observation of the morphological features of the embryo and genetic testing of the embryo. "Preimplantation genetic diagnosis" identifies whether the embryo contains genetic, structural, and/or chromosomal alterations or abnormalities by analysis of polar bodies, blastomeres, or trophectoderm. "Preimplantation genetic screening" involves analysis of polar bodies, blastomeres, or trophectoderm of embryos for detection of aneuploidy, mutation, and/or DNA rearrangement. At least three basic assisted hatching and biopsy techniques are known in the art for diagnosing embryos. These techniques include mechanically creating an incision in the zona pellucida of the embryo using a specialized microsurgical knife or glass needle; chemically digesting a portion of the zona pellucida with acid, such as Tyrode's solution; or removing the zona pellucida using a laser to assist separation of the blastocyst.

In a preferred embodiment, by visual observation of the embryo using microscopy (for example, Nikon Eclipse TE 2000-S microscope), the embryo will display certain determined physical or morphological features simultaneously before it is implanted into the uterus. The state of blastocyst maturity will be determined to be the range II AB-VI AA according to classification of Gardner et al, 1994, incorporated herein by reference, whereby the intracellular mass and the thickness of the trophectoderm layer are classified. Level VI AB represents the highest state of blastocyst maturation, corresponding to a formed blastocyst that hatches from the zona pellucida.

Genetic diagnosis of the embryo can be performed by any techniques known in the art, such as traditional bacterial artificial chromosome (BAC) array CGH and others like it. Microarrays, also referred to as microchip arrays, arrays or biochips, have become widely used for gene expression and other genomic research and provide technical advantages to BAC. A microarray is generally made by printing or synthesizing nucleic acid that is complementary to known sequences in a genome onto a surface. The entire genome of an organism or parts thereof can be evaluated by hybridizing amplified and fluorescently labeled DNA (deoxyribonucleic acid) to the array. U.S. patent application Ser. No. 12/587,406, incorporated herein by reference in its entirety, discloses methods of in vitro fertilization wherein preimplantation genetic diagnosis of all 24 chromosomes of the IVF embryo is performed by whole genome amplification and microarray analyses of polymorphisms. The method involves biopsying the IVF embryo to remove one or more cells and extracting nucleic acid from the cells. Performing genome amplification then allows the gathering of genetic information of the embryo in order to predict the genetic normalcy of the embryo based on the obtained genetic information. This technique also makes it possible to determine the karyotype of the embryo. After the embryos are analyzed, they are ranked for potential implantation into the uterus. In embodiments were the embryos are genetically analyzed, one or more desirable embryos for implantation into the uterus are selected based on genetic predictions.

Kinetic diagnosis of the embryo is another important procedure available for choosing the embryos most desirable, most healthy, for embryo transfer. One tool available is Primo Vision time-lapse embryo monitoring system (Vitrolife AB, Goteborg, Sweden). Prima Vision is a camera and computer system that is designed to capture images of embryos, used in in vitro fertilization cycles, as they grow in the incubator. The images, taken by the camera as an embryo develops in a culture dish, are displayed on a computer screen in the laboratory. The computer system not only provides the images of embryos, but also information about their pattern of growth. This information allows embryologists and clinicians to observe healthy development in embryos and to detect any problems in the timing of cell division that might occur during the early stages of growth. The added benefit of Primo Vision is that it allows these observations to be made without removing the embryos from their incubator. This allows the embryos to remain in a controlled environment where they tend to grow faster. According to the invention, the most desirable embryos to be selected for embryo transfer should display the following kinetics criteria: a time factor of 5-12 hours for division from the 2-cell stage to the 3-cell stage; should have 3 cells at 35-40 hours after zygote stage; 5 cells at 48-56 hours after zygote stage; 8 cells to the beginning of the third day of development. All the cells should preferably have the same size, or as close as possible, and the fragmentation level should be not more than 5-10%.

According to the present invention, the oocytes derived from the patient or the fertilized oocytes having developed to transfer-ready embryo stage are preserved during the period of time until the patient's immune system is sufficiently prepared to accept the embryo for gestation, for the requisite period of time needed to suppress the autoimmune response of the patient. Most patients desire to conceive with their own progeny, if possible, and therefore wish to utilize their own oocytes or embryos. Therefore, in most common situations, the oocytes or embryos of the patient need to be preserved.

In a certain segment of women presenting with infertility, the woman is unable to produce eggs or to ovulate, or experiences anovulation or oligo-ovulation, so donor oocyte(s) or donor embryo(s), which are obtained from another female individual, are provided for the in vitro procedure. It is therefore contemplated within the scope of certain embodiments of the invention that the patient will be incepted with embryos that have not been derived from the patient herself, but are derived from a different individual, therefore, a donor oocyte or donor embryo is transferred to the patient for inception.

Also within the scope of the invention are embodiments where eggs or embryo from one species is transferred to a species different than that from which the egg or embryo are derived. For example, an embryo from a donkey may be implanted into the womb of a horse.

However, it will still remain the most common case that preservation of the oocytes or embryos, (usually derived those of the patient, but possibly of another source) will be required. Preservation can be provided by subjecting the oocyte or embryo to low-temperature conditions, such as slow-cooling, rapid freezing and vitrification. Unlike sperm, which has been successfully frozen and used for years, eggs contain a great deal of water, which makes freezing more difficult. When the eggs are frozen, ice crystals can form within the egg. These ice crystals can destroy the cell's structure. To help minimize the amount of ice crystals, scientists would remove some of the water as the egg was slowly frozen. U.S. patent application Ser. No. 10/777,149 describes a method comprising centrifugation of oocytes or embryos, (for example of dogs, cats, pigs, livestock, mice, rats, and monkeys) to polarize cytoplasmic lipid outside the oocyte or embryonic cells, subjecting the oocytes or embryos to low temperature conditions in the presence of a cryoprotectant which results in the freezing of the oocytes or embryos prior to lipid depolarization, followed by low-temperature storage of the frozen oocytes or embryos. However, it has heretofore been found to be impossible to remove all the water, and thus intra- and extra-cellular ice crystal formation cannot be prevented by slow-freezing. Thus, fertilization of oocytes, embryo viability and pregnancy inception for these slow-frozen eggs, once thawed, is low.

Rapid freezing has been attempted with the use of cryoprotectants. A cryoprotectant is a substance that is used to protect biological tissue from freezing damage that results from ice formation. Cryoprotectants operate by increasing the solute concentration in cells. In order to be biologically viable, cryoprotectants must easily penetrate the cells and not be toxic to the cells. Conventional cryoprotectants are glycols such as ethylene glycol, propylene glycol, and glycerol; 2-methyl-2,4-pentanediol (MPD); dimethyl sulfoxide (DMSO) and sucrose. Glycerol and DMSO have been used for decades by cryobiologists to reduce ice formation in sperm and embryos that are cold-preserved in liquid nitrogen. It has been found that mixtures of cryoprotectants have less toxicity and are more effective than single-agent cryoprotectants. A mixture of formamide with DMSO, propylene glycol, and a colloid was for many years the most effective of all artificially created cryoprotectants. Many cryoprotectants also function by forming hydrogen bonds with biological molecules as water molecules are displaced. Hydrogen bonding in aqueous solutions is important for proper protein and DNA function. Thus, as the cryoprotectant replaces the water molecules, the biological material retains its native physiological structure and function, although they are no longer immersed in an aqueous environment More recently, the process of vitrification, a process of freezing and solidification without ice crystal formation, has been applied to preserving oocytes and embryos, biological tissues, and organs for transplant and cryonics. Some cryoprotectants function by lowering the glass transition temperature of a solution or of a material. In this way, the cryoprotectant prevents actual freezing, and the solution maintains some flexibility in a glassy phase. Although slow and rapid freezing are operable, vitrification is the preferred method of preservation of the oocytes or embryos pursuant to the method of the invention. During vitrification, the oocyte or embryo is frozen quickly enough that ice crystals do not have time to form. Any known vitrification technique can be utilized within the method of the invention for preservation and storage. Commonly, the oocyte or embryo is first placed in a bath with a lower concentration antifreeze, along with sucrose to draw water out of the oocyte or embryo. The oocyte is then placed in a high-concentrated bath of anti-freeze for less than one minute, while being instantaneously frozen. One example of the vitrification process operable within the process of the invention involves placing embryos maintained in MEDICULT® medium at 37° C., then placing the embryos into the medium at 22-24° C., which is then placed in a special cryotop or cryoleaf carrier into liquid nitrogen.

According to the IVF method of the invention, the female patient is ready to continue with embryo transfer when it is determined that the patient's autoimmune system has regained hormonal balance. At such time, the cryopreservation of the eggs or the IVF-derived embryos is terminated. The oocyte(s) or embryo(s) are removed from the antifreeze solution and are thawed. Once thawed, an unfertilized egg can be fertilized by any of the techniques described above by an assisted reproductive technology that injects a sperm directly into an egg. The embryo is thawed by withdrawing it from the liquid nitrogen solution, placing into a solution having a temperature of approximately 37° C., washing at room temperature, placing again into a solution of 37° C., placing into a culture medium, then placing into an incubator held at a temperature similar to the internal temperature of a female uterine cavity, from 36.8 to 37.2° C. for a period of from 5 to 24 hours, most preferably at a temperature of 37.1° C. for 5 to 7 hours.

In the final stage of the process of the invention is the procedure by which one or more embryos are introduced into the patient in an attempt to produce pregnancy. This procedure is termed "embryo transfer" and involves transfer of the embryo into the uterus, the uterine cavity or the fallopian tubes. Embryo transfer typically involves placing the selected embryos through the cervix into the uterine cavity of the female patient using a small, soft catheter and guided by an ultrasound probe. As provided above, according to the method of the invention, preferably at least 24 hours prior to embryo transfer, the endometrium of the uterus of the patient is prepared by injecting a composition of PBMCs into the uterine cavity using an appropriate catheter for delivery. The embryo is typically maintained within an embryo transfer medium, for example, Medicult® UTM medium, and can contain HAS, recombinant human insulin, gentamicin.

It is yet an additional aspect of the present invention that pregnancy inception is further promoted by introducing histocompatibility antigens such as soluble human leukocyte antigen G (sHLA-G) into the system which function as "friend-or-foe communicators" to allow positive recognition and acceptance of the embryo by the woman's immune system. HLA-O, the precursor to its soluble form, sHLA-G, has been detected by researchers on preimplantation embryos and in the surrounding culture media obtained during IVF studies. These finding suggested that sHLA-G is involved from the early stages of pregnancy. Also suggested is the potential of sHLA-G to operate as an indicator of embryo quality. [Menicucci et al. 1999]. One study suggests that sHLA-G levels in preimplantation embryo supernatants can be quantified and suggest positive results with likelihood of pregnancy by acting as a useful indicator of embryo quality which can be used in conjunction with morphological testing to in embryo selection criteria to increase probability of successful implantation. In one embodiment, s-HLA-G is added to the embryo transfer medium, with a preferred concentration measurement in the embryo transfer medium in the range of 0.175 to 0.350 optical density (OD), where OD means the optical density measured at a wavelength in the range of 400 to 450 nm, more specifically at a wavelength of 405 nm. The procedure for determining the concentration of sHLA through measurement of optical density is comprehensively described in number of publications. [See, for example, S. Marti et al., 2007]. The s-HLA-G is added to the embryo transfer medium, and the embryo is then cultured in said medium, for 5 to 20 minutes, and more preferably for approximately 10 minutes immediately prior to transfer of the embryo into the uterus.

A related aspect of the invention provides a method of growing, repairing, engineering, restoring, or otherwise treating a target tissue of a patient by growing the target tissue in the presence of the PBMC composition according to the process set forth in this disclosure. The tissue is grown by introducing the tissue in the presence of the cultured PBMCs or by culturing with the use of the combined PBMC composition of cultured and fresh PBMCs. Both in vivo and in vitro processes are contemplated. One embodiment of such method is that the target tissue is the endometrium of the uterus of a female patient. However, as disclosed in U.S. Pat. Nos. 7,795,018 and 8,216,838 to Kuwana et al., the PBMCs are recognized as multipotent cells which are very suitable for cell transplantation for organ regeneration including bone, cartilage, skeletal muscle, fat, cardiac muscle, vascular, endothelial and neurons. Therefore, the process, the culture medium and the composition of the invention comprising the combination of both cultured and fresh PBMCs of the present invention can be expanded well beyond the boundaries of IVF treatment and treatment of the endometrium to applications involving the growth, repair and engineering of other tissues that are capable of being treated by PBMCs.

It is to be noted herein that the concept and practice of this invention is most relevant to humans but is applicable to embryo implantation in a wide variety of animals. This invention is not limited to human in vitro fertilization or embryo implantation using autoimmune system delay with use PBMC compositions. For example, the technique can be used with animals such as murine animals including the brown rat and the household mouse; with companion animals including dogs and cats; and with domestic livestock animals, such as pigs, horses, donkeys, goats, sheep, llamas and alpacas, among others in order to increase live birth rates of such animals. Such increases will have significant financial implications in the livestock industry and social implications in the areas of scientific and medical research and development.

While the invention is generally defined as above, persons skilled in the art will appreciate that it is not limited thereto and includes embodiments of which the following examples provide further description. It is to be understood that other specific functional modifications may be made within the scope of the art without departing from the scope of the present invention. The advantages of the invention are demonstrated by the examples below, which are set forth to illustrate the methods and composition of the invention and are intended to be purely exemplary of the principles and applications of the invention and are not to be viewed as limiting in its scope.

EXAMPLES

The examples below illustrate the present invention. A study was performed to examine and compare two IVF procedures. The first procedure was termed the "Fresh-IVF" method and the second procedure was termed the "Cryo-IVF" method. Statistical comparison of the clinical results was performed in order to examine the effect in pregnancy rates on women presenting with infertility of delaying embryo or blastocyst implantation into the uterine cavity of the woman after oocyte retrieval. The terms "pregnancy rate", "clinical pregnancy rate" and "implantation rate" are used interchangeably herein and refer to the number of clinical pregnancies expressed per 100 embryo transfer cycles. Further investigated was the effect of intrauterine peripheral mononuclear blood cell (PMBC) administration on pregnancy rates for both "Fresh-IVF" and "Cryo-IVF" procedures.

Subjects: One-hundred and eighty (180) women presenting with infertility in total were examined. Prior to the present study, each of the patients had previously undergone two or more unsuccessful "Fresh-IVF" treatments and at least one failed "Cryo-IVF" treatment before participating in the study herein. The women were divided into 2 groups of 90 women per group. The average age of the women in the Group 1 was 35.5±3.4 years. The average age of the patients in the Group 2 was 36.5±5.5 years. The subjects were prepared as follows:

IVF Procedure: Standard IVF protocol using a-GnRH (gonadotropin-releasing hormone) for controlled ovary stimulation was applied to patients in both groups. The period of ovary stimulation for every patient was between 10 to 12 days. The average size of follicles was measured to be approximately 18 mm at the moment of transvaginal puncture. Gonal, Menopur, Choragon were applied to patients of both groups for maintaining the luteal phase. In general, 10 to 12 eggs were retrieved from each patient. Not less than 80% of obtained oocytes were mature enough to be fertilized (stage of maturation MII as determined by Gardner's classification).

Following oocytes retrieval, the oocytes were cultured in Universal IVF Medium (MEDICULT® available from Origio A/S Corporation, Denmark) having $CO_2$ concentration in the range of 5.5-5.7% at a temperature of 36.8-37.1° C. The oocytes were then fertilized via both ICSI and standard IVF procedure. The technique was chosen taking into account sperm indices, the age of the patient, the experience of previous IVF attempt with negative result. In cases of standard IVF procedure, spermatozoa were added to oocytes in UniIVF medium. The zygotes developed the next day were placed into ISM-1 medium. In cases where oocytes were obtained by transvaginal puncture, the oocytes were placed into UniIVF medium. Following fertilization by ICSI procedure, the eggs were placed into ISM-1 immediately. The embryos were cultured in MEDICULT® Universal IVF Medium during the first three days for cleavage embryo development and in MEDICULT® BlastAssist Medium during the fourth and fifth day of culture until blastocyst formation. Embryo transfer was performed using MEDI-CULT® UTM Medium.

Vitrification: Vitrification was applied to the blastocysts or embryos on day 5 of development utilizing the standard MEDICULT® method. The embryos were placed in specified solutions to remove as much of the water as possible. The embryos were placed on cryotop carriers into liquid nitrogen. Not more than two embryos were placed onto one carrier. The frozen embryos were stored during the waiting a period of three (3) months to one year.

PBMC Preparation: Peripheral blood mononuclear cells (PBMCs) were extracted from each patient. The first portion of the PBMCs was taken from the patient at the day of oocytes receive in the "Fresh-IVF" protocols or three days earlier then the embryos were transferred to the uterus in the "Cryo-IVF" protocols. Initially, 10 mL of peripheral blood were taken from each patient. The entire quantity (10 mL) of the peripheral blood was mixed with 10 mL of MEDI-CULT® RPMI 1640 medium with L-glutamine and sodium bicarbonate forming a combined volume of 20 mL of diluted blood. Lymphocyte separation medium (density gradient medium) was then used to separate the PBMCs from the blood. A volume of 7 mL of diluted blood was layered onto 3 mL of the density gradient medium. After layering, centrifugation of the layered blood was performed at a speed of 1500 rounds per minute for 30-35 min to yield the PBMCs. The PBMCs thus obtained were washed twice in RPMI by centrifugation for 10 min at a speed of 1600 rounds per minute at 4° C. The washed PBMCs were transferred to the culture medium. The culture medium constituted a mixture of RPMI 1640 medium with L-glutamine and sodium bicarbonate with addition of human chorionic gonadotropin (hCG) and human recombinant albumin (from Sigma-Aldrich Co., LLC). The conditions of culture were maintained at 5.0% CO2 and 37° C. The period of PBMCs culture was 48-52 hours. After 48-52 hours, an additional portion of whole blood was taken from the same patient. Additional PBMCs were extracted by the same method. The second batch of the PBMCs were combined with the cultured PBMCs and the mixture was transferred to the uterine cavity of the patient via catheter. The procedure is carried out quickly, in a total of 10-15 minutes. The volume of the total PCMB mixture for intrauterine application for each patient was in the range 0.2-0.3 mL.

Embryo Thawing and Transfer: For each patient, two blastocysts were selected for embryo transfer. Thawing was performed using standard MEDICULT® protocol. The embryos were removed from the liquid nitrogen and placed into a solution of 37° C., then washed with several solutions at room temperature, the placed again into a solution at 37° C., then placed into culture medium into an incubator at a temperature of a temperature of 37.1° C. for 6 hours. The embryos were cultured in BlastAssist MEDICULT® Medium or 3-4 hours after thawing. The embryos were then placed into MEDICULT® UTM medium for approximately 15 minutes. Embryo transfer was performed with use of MEDICULT® UTM medium via Cook® Medical ultrasound control catheters.

IVF Procedure: Both groups of women underwent IVF treatment. The IVF procedure performed on Group 1 did not involve the use of PCMBs; whereas the IVF procedure for Group 2 was carried out with the use of PBMCs. The course of treatment for each group of women included two stages—a "Fresh-IVF" cycle and a "Cryo-IVF" cycle, as described herein. On the day of embryo transfer, the endometrium size was measured at 9-11 mm in both groups of patients. After embryo transfer, all patients were administered progesterone as is standard during IVF treatment in order to prepare the endometrium for embryo implantation. Implantation of the embryo was confirmed by blood tests on b-hCG performed two weeks after embryo transfer. Clinical pregnancy was confirmed by ultrasound examination three weeks after embryo transfer.

Both groups of women underwent one "Fresh-IVF" cycle with the transfer of two blastocysts. Each patient was tested for pregnancy. Failure resulted when the testing showed an absence of clinical or biochemical pregnancy. In those cases where the "Fresh-IVF" cycle failed to result in a successful implantation of the embryo, a "Cryo-IVF" cycle was performed in which frozen embryos were introduced into the uterine cavity of the patient after a time-delay period of between 2-3 menstrual cycles after the negative "Fresh-IVF" cycle, which measured at about three (3) months after the day on which the oocytes were retrieved from the ovaries of the patient.

The women in Group 1 did not receive any application of PCMBs; the women in Group 2 received a treatment of PBMCs immediately after the end of the waiting period. During the "Fresh-IVF" cycles, the PBMCs were administered into the uterus of each subject on the second day of embryo culture at 48-52 hours after egg retrieval. During the "Cryo-IVF" cycles, the PBMCs were administered to uterus about 24 hours before embryo transfer.

Results: The group of patients undergoing Fresh-IVF treatment without PBMCs, resulted in an implantation rate of 22.2% (20 clinical pregnancies after 90 ET). The use of PMBCs during the "Fresh-IVF" method caused an increase in the implantation rate up to 31.1% (28 clinical pregnancies after 90 ET). In the group of women undergoing attempts via "Cryo-IVF" treatment (time delay lasting at least 3 months for both Group 1 and Group 2), the implantation rate without intrauterine application of PBMCs was 21.4% (15 clinical pregnancies after 70 ET), while after application of PBMCs, the implantation rate was almost two times higher 41.9% (26 clinical pregnancies after 62 ET). The total success rate for Group 1 (90 patients without application of PBMCs) was 38.9% (35 clinical pregnancies). The total success rate for Group 2 (90 patients with application of PBMCs) was 60.0% (54 clinical pregnancies). The clinical results of the study are presented in Table 1 below. The abbreviation "ET" indicates "embryo transfers".

TABLE 1

Implantation rates in "Fresh-IVF" and "Cryo-IVF" cycles, with and without administration of PBMCs to the patient.

| | Clinical Pregnancy Rate | |
|---|---|---|
| | Group 1 (without PBMCs) | Group 2 (with PBMCs) |
| Fresh-IVF | 22.2% (20 pregnancies after 90 ET) | 31.1% (28 pregnancies after 90 ET) |
| Cryo-IVF | 21.4% (15 pregnancies after 70 ET) | 41.9% (26 pregnancies after 62 ET) |
| Total | 38.9% (35 pregnancies for 90 patients) | 60.0% (54 pregnancies for 90 patients) |

Table 1 demonstrates the increased pregnancy rate obtained when compared to traditional IVF through the use of the woman's own PBMCs through the preparation of uterus prior to embryo transfer. It is further demonstrated that combining the delayed or "Cryo-IVF" technique together with preparation for inception of a patient's uterus by the administration of the woman's own PBMCs during the in vitro fertilization process produces a significant increase in the rate of pregnancy of infertile women as compared to previously-known IVF procedures, possibly as a synergistic result both of allowing the female patient's autoimmune system to regain hormonal balance and allowing the inception process to be realized in a uterine cavity having an enhanced ability for embryo implantation.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A method for transferring at least one embryo after IVF comprising administering to a patient in need thereof a composition produced by a method comprising:

obtaining a first portion of PBMCs from blood of a patient which was taken at least two months or two cycles of ovulation after a last immune system-influencing or endocrine system-influencing event, propagating the first portion of PBMCs in a culture medium containing a promoting agent that is human chorionic gonadotropin (HCG) or an HCG equivalent in the presence of 4.8 to 6.0% carbon dioxide ($CO_2$) and culturing for a period of time sufficient to obtain a desired number of cultured PBMCs;

wherein the immune-system-influencing event or the endocrine-system-influencing event comprises controlled ovary stimulation or oocyte retrieval during a cycle of in vitro fertilization (IVF) treatment;

further comprising extracting a second, fresh portion of PBMCs from the blood of the patient at least two months or two cycles of ovulation after a last immune system-influencing or endocrine system-influencing event, combining the cultured PBMCs and the second, fresh portion of PBMCs, and obtaining said composition;

wherein the first portion of the PBMCs is derived from blood collected from the patient at a first time between (i) transferring the at least one embryo into the uterus of the patient and (ii) three days prior to transferring the at least one embryo into the uterus of the patient, wherein the second portion of the peripheral blood mononuclear cells is derived from blood collected from the patient at a second time between (i) transferring the at least one embryo into the uterus of the patient and (ii) three days prior to transferring the at least one embryo into the uterus of the patient, and wherein the second time is after the first time and the second time is 20 to 72 hours before the embryo/s transfer into the patient's uterus.

2. The method of claim 1, further comprising extracting at least one additional fresh portion of PBMCs from the blood of the patient, combining the first portion, second, fresh portion and the at least one additional fresh portion of PBMCs, and propagating said PBMCs for a period of time sufficient to obtain a desired number of PBMCs.

* * * * *